(12) United States Patent
Barbato (10) Patent No.: US 8,854,627 B2
(45) Date of Patent: *Oct. 7, 2014

(54) ELECTRONICALLY SCANNED OPTICAL COHERENCE TOMOGRAPHY WITH FREQUENCY MODULATED SIGNALS

(71) Applicant: Boston Scientific SciMed, Inc., Maple Grove, MN (US)

(72) Inventor: Louis J. Barbato, Franklin, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/015,131

(22) Filed: Aug. 30, 2013

(65) Prior Publication Data

US 2014/0024947 A1 Jan. 23, 2014

Related U.S. Application Data (60) Continuation of application No. 12/105,910, filed on Apr. 18, 2008, now Pat. No. 8,526,004, which is a continuation of application No. 11/284,684, filed on Nov. 21, 2005, now abandoned, which is a division of application No. 10/690,948, filed on Oct. 21, 2003, now Pat. No. 7,181,267, which is a division of application No. 09/906,903, filed on Jul. 16, 2001, now Pat. No. 6,728,571.

(51) Int. Cl.
*G01B 9/02* (2006.01)
*A61B 5/00* (2006.01)

(52) U.S. Cl.
CPC .......... *A61B 5/0066* (2013.01); *G01B 9/02002* (2013.01); *G01B 9/02028* (2013.01); *G01B 9/02091* (2013.01); *A61B 5/6852* (2013.01)

USPC .......................................................... 356/484

(58) Field of Classification Search
USPC .......................................................... 356/484
See application file for complete search history.

(56) References Cited

U.S. PATENT DOCUMENTS

| | | | |
|---|---|---|---|
| 3,714,607 A | 1/1973 | Cutler | |
| 4,697,926 A | 10/1987 | Youngquist et al. | |

(Continued)

FOREIGN PATENT DOCUMENTS

| | | |
|---|---|---|
| EP | 0578400 A2 | 1/1994 |
| EP | 1090582 A1 | 4/2001 |

(Continued)

OTHER PUBLICATIONS

"Optical Coherence Tomography: Principles, Instrumentation and Applications," Abstract only, presented at IEEE Society XXIst Australian Conference on Optical Fiber Technology, Dec. 1996, Brisbane, Australia, 4 pages.

(Continued)

*Primary Examiner* — Jonathan Hansen
(74) *Attorney, Agent, or Firm* — Lowe Graham Jones PLLC; Bruce E. Black (57) ABSTRACT

An improved Optical Coherence Domain Reflectometry (OCDR) system is provided. One embodiment of this OCDR system outputs a detector signal carrying image depth information on multiple modulation frequencies, where each modulation frequency corresponds to a different image depth. The image depth information from the detector signal may be resolved by tuning to the desired modulation frequency. Another system for imaging body tissue uses multiple frequency modulators such that the light beam does not travel from an optical fiber to free space.

20 Claims, 7 Drawing Sheets

(56) References Cited

U.S. PATENT DOCUMENTS

| | | | |
|---|---|---|---|
| 4,805,627 A | | 2/1989 | Klingenbeck et al. |
| 4,810,875 A | | 3/1989 | Wyatt |
| 4,818,064 A | | 4/1989 | Youngquist et al. |
| 5,321,501 A | * | 6/1994 | Swanson et al. ............. 356/479 |
| 5,363,849 A | | 11/1994 | Suorsa et al. |
| 5,365,770 A | | 11/1994 | Meitzler et al. |
| 5,383,467 A | | 1/1995 | Auer et al. |
| 5,397,548 A | | 3/1995 | Kritzler et al. |
| 5,453,575 A | | 9/1995 | O'Donnell et al. |
| 5,459,570 A | | 10/1995 | Swanson et al. |
| 5,465,147 A | * | 11/1995 | Swanson ...................... 356/497 |
| 5,523,788 A | | 6/1996 | Kannegundla et al. |
| 5,538,004 A | | 7/1996 | Bamber |
| 5,588,434 A | | 12/1996 | Fujimoto |
| 5,640,960 A | | 6/1997 | Jones et al. |
| 5,692,507 A | | 12/1997 | Seppi et al. |
| 5,699,798 A | | 12/1997 | Hochman et al. |
| 5,715,825 A | | 2/1998 | Crowley |
| 5,752,518 A | | 5/1998 | McGee et al. |
| 5,830,145 A | * | 11/1998 | Tenhoff ........................ 600/463 |
| 5,892,583 A | | 4/1999 | Li |
| 5,904,651 A | | 5/1999 | Swanson et al. |
| 5,905,572 A | | 5/1999 | Li |
| 5,943,133 A | | 8/1999 | Zeylikovich et al. |
| 5,949,929 A | | 9/1999 | Hamm |
| 5,994,690 A | | 11/1999 | Kulkarni et al. |
| 6,002,480 A | | 12/1999 | Izatt et al. |
| 6,006,128 A | | 12/1999 | Izatt et al. |
| 6,111,645 A | | 8/2000 | Tearney et al. |
| 6,134,003 A | * | 10/2000 | Tearney et al. ............... 356/479 |
| 6,141,577 A | | 10/2000 | Rolland et al. |
| 6,152,977 A | | 11/2000 | D'Evelyn |
| 6,196,226 B1 | | 3/2001 | Hochman et al. |
| 6,198,540 B1 | * | 3/2001 | Ueda et al. .................... 356/479 |
| 6,233,480 B1 | | 5/2001 | Hochman et al. |
| 6,241,672 B1 | | 6/2001 | Hochman et al. |
| 6,256,102 B1 | | 7/2001 | Dogariu |
| 6,264,610 B1 | | 7/2001 | Zhu |
| 6,363,033 B1 | | 3/2002 | Cole et al. |
| 6,381,490 B1 | | 4/2002 | Ostrovsky |
| 6,390,978 B1 | | 5/2002 | Irion et al. |
| 6,390,982 B1 | | 5/2002 | Bova et al. |
| 6,485,413 B1 | | 11/2002 | Boppart et al. |
| 6,491,647 B1 | | 12/2002 | Bridger et al. |
| 6,522,913 B2 | | 2/2003 | Swanson et al. |
| 6,529,770 B1 | | 3/2003 | Grimblatov |
| 6,611,339 B1 | | 8/2003 | Yang et al. |
| 6,671,540 B1 | | 12/2003 | Hochman |
| 6,697,654 B2 | | 2/2004 | Lorenz et al. |
| 6,728,571 B1 | * | 4/2004 | Barbato ........................ 600/478 |
| 6,834,238 B1 | | 12/2004 | Hochman |
| 6,847,454 B2 | | 1/2005 | Crowley et al. |
| 7,006,231 B2 | | 2/2006 | Ostrovsky et al. |
| 7,058,211 B2 | | 6/2006 | Barbato |
| 7,181,267 B2 | | 2/2007 | Barbato |
| 8,526,004 B2 | * | 9/2013 | Barbato ........................ 356/484 |
| 2006/0106320 A1 | | 5/2006 | Barbato |

FOREIGN PATENT DOCUMENTS

| | | |
|---|---|---|
| JP | 6511312 | 12/1994 |
| JP | 2000503237 | 3/2000 |
| JP | 2001500762 A | 1/2001 |
| JP | 2002514301 A | 5/2002 |
| WO | 9219930 A1 | 11/1992 |
| WO | 9732182 A1 | 9/1997 |
| WO | 9811823 A1 | 3/1998 |
| WO | 9825105 A1 | 6/1998 |
| WO | 9838907 A1 | 9/1998 |

OTHER PUBLICATIONS

Jiang, Y., "IV.12—Avalanche Photodiodes (APD's)?" The unusual Diode FAQ, Avtech Electrosystems Ltd., http://www.avtechpulse.com/faq.html/IV.12/, Jul. 13, 2001, 3 pages.

Kuz'Minov, Y. S., "Lithium Niobate Crystals," Abstracts and Contents only, May 1999, 180 pages, http://www.demon.co.uk/cambsci/book10.htm.

LightLab Imaging, LLC, "Advantages of OCT" and "What is OCT?" LightLab Optical Coherence Tomography; http://www.lightlabimaging.com/, 2000, 3 pages.

Pitris, C. et al., "High Resolution Imaging of Neoplastic Changes in Gynecological Tissue Using Optical Coherence Tomography," Abstract only, American Society of Clinical Oncology, 1998, http://www.asco.org/prof/me/html/98abstracts/gync/m_1434.htm.

Zeylikovich, I. et al., "Nonmechanical Grating-Generated Scanning Coherence Microscopy," Optics Letters, vol. 23, No. 23, Dec. 1, 1998, pp. 1797-1799.

Warren, S. et al., "Combined Ultrasound and Fluorescence Spectroscopy for Physico-checmical Imaging of Atherosclerosis," IEEE Transactions on Biomedical Engineering, IEEE Inc., New York, NY, US, vol. 42, No. 2, Feb. 1995.

International Search Report for International Patent Application No. PCT/US02/32277 mailed Dec. 19, 2002.

International Search Report for International Patent Application No. PCT/US02/22628 mailed Feb. 14, 2003.

International Search Report for International Patent Application No. PCT/US02/20241 mailed Jul. 24, 2003.

Official Communication for U.S. Appl. No. 09/909,357 dated Aug. 11, 2005.

Official Communication for U.S. Appl. No. 10/020,040 dated Jul. 31, 2003.

Official Communication for U.S. Appl. No. 10/020,040 dated Jan. 2, 2004.

Official Communication for U.S. Appl. No. 10/020,040 dated Jun. 14, 2004.

Official Communication for U.S. Appl. No. 10/690,948 dated May 9, 2005.

Official Communication for U.S. Appl. No. 11/284,684 dated Jun. 4, 2007.

Official Communication for U.S. Appl. No. 11/284,684 dated Oct. 18, 2007.

Official Communication for U.S. Appl. No. 12/105,910 dated Mar. 27, 2012.

Official Communication for U.S. Appl. No. 12/105,910 dated Aug. 23, 2012.

* cited by examiner

ELECTRONICALLY SCANNED OPTICAL COHERENCE TOMOGRAPHY WITH FREQUENCY MODULATED SIGNALS

CROSS REFERENCE TO RELATED APPLICATIONS

This application is a continuation of U.S. patent application Ser. No. 12/105,910 filed Apr. 18, 2008, now U.S. Pat. No. 8,526,004, which is a continuation of U.S. patent application Ser. No. 11/284,684 filed Nov. 21, 2005, now abandoned, which is a divisional of U.S. patent application Ser. No. 10/690,948 filed Oct. 21, 2003, now U.S. Pat. No. 7,181,267, which is a divisional of U.S. patent application Ser. No. 09/906,903 filed Jul. 16, 2001, now U.S. Pat. No. 6,728,571, all of which are incorporated herein by reference.

FIELD OF THE INVENTION

The invention relates generally to a method and system for making optical measurements, and in particular, to a method and system for making optical measurements for a catheter-based imaging system such as Optical Coherence Domain Reflectometry (OCDR).

BACKGROUND OF THE INVENTION

Ultrasound medical imaging is often used to produce images of blood vessels and surrounding tissue. To image a blood vessel and surrounding tissue, an Intravascular Ultrasound (IVUS) catheter is typically used. The IVUS catheter comprises an elongated member and an ultrasound transducer located at a distal end of the elongated member. The elongated member is inserted into the blood vessel, and the ultrasound transducer is positioned at a desired location in the blood vessel. An ultrasound transducer is designed to transmit a specific resonant frequency, e.g., when it is excited by a pulse. The excite pulse signal causes the ultrasound transducer to emit ultrasound waves in the blood vessel. A portion of the emitted ultrasound waves is reflected back to the ultrasound transducer at tissue boundaries in the blood vessel and the surround tissue. The reflected ultrasound waves induce an echo signal at the ultrasound transducer. The echo signal is transmitted from the ultrasound transducer to an ultrasound console, which typically includes an ultrasound image processor and a display. The ultrasound console uses the received echo signal to image the blood vessel and the surrounding tissue.

In order to produce a radial cross-sectional image of a blood vessel and surrounding tissue, the ultrasound transducer is typically rotated along the axis of the elongated member. As the ultrasound transducer is rotated, the ultrasound transducer emits ultrasound waves in different radial directions. The resulting echo signals from the different radial directions are processed by the ultrasound console to produce a radial cross-sectional image of the blood vessel and the surrounding tissue. Alternatively, the ultrasonic transducer may be mounted in an assembly together with a reflective member (mirror), where the transducer emits ultrasonic energy in a substantially axial direction and the mirror is oriented to deflect the emitted ultrasonic energy in a radial direction.

The echo signal is a serial amplitude modulated signal, in which the amplitude of the signal varies with time. A typical echo signal has a time length of 8 µs, which corresponds to an image depth of approximately 6 millimeters from the ultrasound transducer. The echo signal carries both image brightness information and image depth information, where depth may be taken with respect to the ultrasound transducer. The image brightness information is provided by the amplitude of the echo signal. The image depth information is provided by the time position within the echo signal. For example, an earlier time position in the echo signal corresponds to a lower image depth than a later time position in the echo signal. This is because an ultrasound wave that is reflected back to the ultrasound transducer from a shallower depth reaches the ultrasound transducer before an ultrasound wave that is reflected back to the ultrasound transducer from a deeper depth. As a result, the ultrasound wave that is reflected back to the ultrasound transducer from the shallower depth has a shorter propagation delay time, which translates into an earlier time position in the echo signal.

Another imaging technique used to produce images of blood vessels and surrounding tissue is Optical Coherence Domain Reflectometry (OCDR). To image a blood vessel using OCDR, a fiber-optic catheter is inserted into the blood vessel. A proximal end of the fiber-optic catheter is coupled to an OCDR system. In the OCDR system, a laser generates a source beam. A beam splitter splits the source beam into a reference beam and a sample beam. The reference beam is diffracted by a diffraction grating into a diffraction beam. The sample beam is transmitted through the fiber-optic catheter and emitted in the blood vessel at a distal end of the catheter. Typically, the distal end of the catheter includes a prism for directing the sample beam into the blood vessel. A portion of the sample beam is reflected back to the distal end of the catheter by the blood vessel and the surrounding tissue. The reflected sample beam is transmitted to the OCDR system through the fiber-optic catheter. In the OCDR system, the reflected beam is mixed with the diffraction beam to produce a coherence-domain interference pattern, which is detected by an array of photo detectors.

The resulting interference pattern provides both image brightness information and image depth information, where depth may be taken with respect to the distal end of the catheter. The image brightness information is provided by the light intensity of the interference pattern. The image depth information is provided by the spatial position within the interference pattern. This is because the portion of the sample beam that is reflected back to the catheter from a certain depth in the body constructively interferes with the diffraction beam at a certain spatial position. Typically, the photo detectors of the photo array are arranged so that each photo detector detects the light intensity of the interference pattern at a certain spatial position within the interference pattern. Thus, the output of each photo detector provides image brightness information for a certain image depth. The photo array outputs parallel channels, where each parallel channel corresponds to the output of one of its photo detectors. The parallel channels of the photo array are inputted to an OCDR image processor to produce an image of the blood vessel and the surrounding tissue.

An advantage of the above-described OCDR system is that the array of photo detectors is able to capture image brightness information at multiple image depths in one instance. This enables the OCDR system to produce images at true video rates, e.g., 30 frames per second.

Optical coherence tomography (OCT) is an optical imaging technique, which achieves non-invasive, cross-sectional imaging of microscopic biological structures. OCT is analogous to ultrasound imaging, only measuring the intensity of backscattered infrared light rather than sound. It can be implemented using high-speed fiber optics, which makes OCT compatible for interfacing with fiber optic endoscopes used for catheter-based imaging within the vascular system.

Mechanical OCT systems use a mirror mounted to a piezoelectric material to achieve mechanical scanning of depth information. However, the speed of these systems are limited by mechanical factors such as mass, the electromechanical properties of the piezoelectric material and the need to scan at a constant velocity. These limitations translate into scanning rates that are considerably slower than true video rate, such that real time viewing cannot be achieved.

In grating generated OCT systems, depth information is spatially translated across a beam of light using a diffraction grating that functions as a series of stepped mirrors. Each "mirror" interacts spatially with light reflected from a sample producing information from multiple points of depth. The parallel depth information is then captured electronically with an array of parallel photoelements. Unlike mechanical OCT systems, grating generated OCT systems can achieve video rates if fast electronic processing is used. However, grating generated OCT systems require a large number of parallel electronic channels, which are very large, complex and power consuming.

Therefore, there exists a need for an OCT system that utilizes a single electronic channel yet still achieves video rate scanning speeds.

SUMMARY OF THE INVENTION

The invention relates to an OCDR system that outputs a detector signal which carries image depth information on multiple modulation frequencies, where each modulation frequency preferably corresponds to a different image depth.

A first, separate aspect of the invention is an OCDR system which outputs a detector signal which carries image depth information on multiple modulation frequencies, where each modulation frequency corresponds to a different image depth.

A second, separate aspect of the invention is an OCDR system which outputs a detector signal which carries image depth information on multiple modulation frequencies such that the image depth information from the detector signal may be resolved by tuning to the desired modulation frequency.

A third, separate aspect of the invention is an OCDR system which has a combined signal having a plurality of modulated frequency signals, where each modulated frequency signal corresponds to a different aspect of the image.

A fourth, separate aspect of the invention is an OCDR system which has a combined signal having a plurality of modulated frequency signals, where each modulated frequency signal corresponds to a different image depth.

A fifth, separate aspect of the invention is an OCDR system which allows a combined beam to focus onto a single light detector.

A sixth, separate aspect of the invention is an OCDR system which enables the use of avalanche mode photodiodes.

A seventh, separate aspect of the invention is an OCDR system which has an interferometer with multiple modulators having no transition from fiber optic to free space.

An eighth, separate aspect of the invention is a method for imaging body tissue comprising the steps of frequency modulating image depth information onto a signal and outputting the signal A ninth, separate aspect of the invention is a method for imaging body tissue comprising the steps of frequency modulating image depth information onto a signal, where each modulation frequency corresponds to a different image depth, and outputting the signal.

A tenth, separate aspect of the invention is a method for imaging body tissue comprising the step of providing a combined signal having a plurality of modulated frequency signals, where each modulated frequency signal corresponds to a different aspect of the image.

An eleventh, separate aspect of the invention is a method for imaging body tissue comprising the step of providing a combined signal having a plurality of modulated frequency signals, where each modulated frequency signal corresponds to a different image depth.

A twelfth, separate aspect of the invention is a method for imaging body tissue which allows a combined beam to focus onto a single light detector.

A thirteenth, separate aspect of the invention is a method for imaging body tissue which enables the use of avalanche mode photodiodes.

A fourteenth, separate aspect of the invention is a method for imaging body tissue which uses multiple modulators having no transition between fiber optic and free space.

The invention may include any one of these separate aspects individually, or any combination of these separate aspects.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

Figure 1:
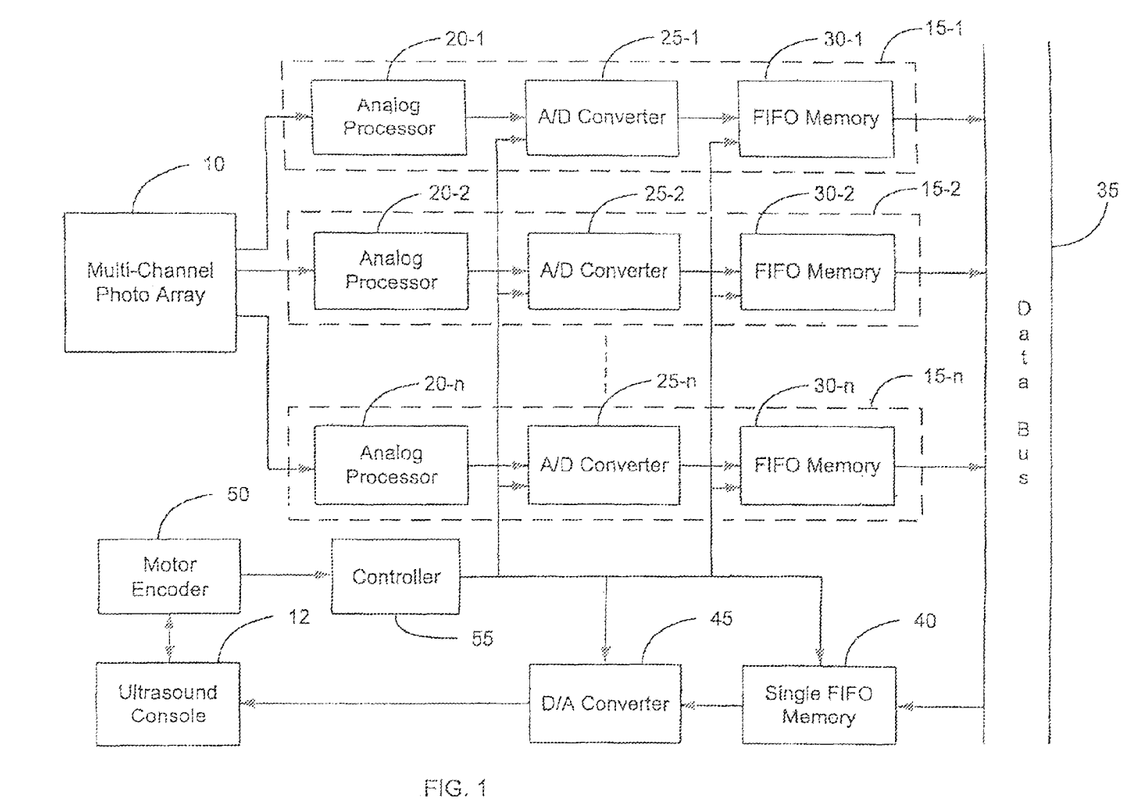
FIG. 1 is a block diagram illustrating an example embodiment of an electronics interface.

FIG. 1 shows an example embodiment of an electronics interface between an OCDR system and an ultrasound console. The electronics interface system is coupled between a multi-channel photo array 10 of an OCDR system and an ultrasound console 12. The photo array 10 comprises a plurality of photo detectors (not shown), e.g., 256 photo detectors. Each photo detector of the photo array 10 outputs a signal carrying image brightness information for a certain image depth. The photo detectors may be photodiodes, Charge Coupled Devices (CCDs), or the like. The photo array outputs a plurality of parallel channels, where each one of the parallel channels corresponds to the output of one of its photo detectors.

The electronics interface includes a plurality of channel processors 15-1 to 15-$n$, where each channel processor 15-1 to 15-$n$ is coupled to one of the parallel channel outputs of the photo array 10. Each channel processor 15-$n$ includes an analog processor 20-$n$, an A/D converter 25-$n$, and a First-In-First-Out (FIFO) memory buffer 30-$n$. For the sake of simplicity, the reference numeral 15-$n$ refers to any of the channel processors 15-1 to 15-$n$; 20-$n$ refers to any of analog processors 20-1 to 20-$n$; 30-$n$ refers to any of FIFO memory buffers 30-1 to 30-$n$. The electronics interface also includes a data bus 35 coupled to the output of each one of the FIFO memory buffers 30-$n$ of the channel processors 15-$n$. The electronics interface further includes a single FIFO memory buffer 40 coupled to the data bus 35, a digital-to-analog (D/A) converter 45 coupled to the output of the single FIFO memory buffer 40, and a controller 55. The output of the D/A converter 45 is coupled to the input of the ultrasound console 12. The controller 55 is also coupled to the analog-to-digital (A/D) converters 25-1 to 25-$n$, the FIFO memory buffers 30-1 to 30-$n$, the single FIFO memory 40 buffer, and the D/A converter 45. The ultrasound console 12 and the controller 55 are each coupled to an ultrasound motor encoder 50 of an ultrasound Patient Interface Unit (PIU). The ultrasound motor 50 outputs encoder pulses which may be spaced, for example, 130 µs apart, to the ultrasound console 12 and the controller 55. The controller 55 uses the received encoder pulses to synchronize the operation of the electronics interface with the ultrasound console 12.

During operation, each photo detector of the photo array 10 outputs a signal, such as a current, to one of the parallel channel outputs of the photo array 10. The signal of each one of the parallel channel outputs may carry image brightness information for a certain image depth, where depth may be taken with respect to a catheter. Each channel processor 15-$n$ of the electronics interface processes one of the parallel channel outputs of the photo array 10. The analog processor 20-$n$ of each channel processor 15-$n$ performs analog processing on the respective parallel channel output signal. The analog processing may include current-to-voltage conversion, signal amplification, bandpass filtering, logarithmic amplification and/or other functions. Logarithmic amplification may be used to translate the signal in the channel processor 15-$n$ to a log scale in order to increase the dynamic range of the signal, for example, to a dynamic range of 100 dB. The output of each analog processor 20-$n$ is coupled to the respective A/D converter 25-$n$.

When the controller 55 receives a first encoder pulse from the motor encoder 50, the controller 55 instructs each A/D converter 25-$n$ to digitize the analog output from the respective analog processor 20-$n$ for a predetermined data acquisition time, such as 100 µs. During this time, each A/D converter 25-$n$ writes its digital data into the respective FIFO memory buffer 30-$n$. At the end of the data acquisition time, the controller 55 instructs the FIFO memory buffers 30-1 to 30-$n$ of the channel processors 15-1 to 15-$n$ to sequentially write their digital data into the single FIFO 40 via the data bus 35. Preferably, the controller 55 instructs the FIFO memory buffers 30-1 to 30-$n$ of the channel processors 15-1 to 15-$n$ corresponding to lower image depths to write their digital data into the single FIFO memory buffer 40 before the FIFO memory buffers 30-1 to 30-$n$ of the channel processors 15-1 to 15-$n$ corresponding to deeper image depths. That way, the digital data from the channel processors 15-1 to 15-$n$ are written into the single FIFO memory buffer 40 in order of increasing image depth.

When the controller 55 receives a second (subsequent) encoder pulse from the motor encoder 50, the controller 55 instructs the single FIFO memory 40 to output its stored digital data, which was taken during the previous encoder pulse, to the D/A converter 45. Preferably, the single FIFO memory buffer 40 outputs the digital data to the D/A converter 40 in the form of a serial digital data sequence in which the digital data in the digital data sequence are arranged in order of increasing image depth. The D/A converter 45 converts the digital data sequence from the single FIFO memory buffer 40 into a serial analog signal, which is outputted to the input of the ultrasound console 12.

Also, during the second encoder pulse, the controller 50 instructs each one of the A/D converters 25-$n$ of the channel processors 15-$n$ to acquire a new set of digital data, which is outputted to the ultrasound console 12 in serial analog form during a third encoder pulse. For each encoder pulse, the electronics interface outputs a serial analog signal to the ultrasound console 12 containing image data that was acquired during a previous encoder pulse. Thus, the electronics interface lags behind the ultrasound console by one encoder pulse, typically 130 µs.

The serial analog signal outputted by the D/A converter 45 may carry both image brightness information and image depth information. The image brightness information is provided by the amplitude of the serial analog signal. The image depth information is provided by the time position within the serial analog signal. An earlier time position in the serial analog signal corresponds to a lower image depth than a later time position in the serial analog signal. This is because the serial analog signal was converted from a serial digital data sequence whose digital data were arranged in order of increasing image depth.

The D/A conversion rate of the D/A converter 40 may be adjusted so that the serial analog signal has approximately the same time length as a typical echo signal, such as 8 µs. In addition, a mixer (not shown), which may be a Double Side-Band Suppressed Carrier (DSBSC) mixer or other kinds of mixers, may be used to adjust, i.e., translate, the frequency of the serial analog signal before it is inputted to the ultrasound console 12. For example, the mixer may be used to adjust the frequency of the serial analog signal to the frequency of a typical echo signal that the ultrasound console 12 is configured to receive.

Therefore, the electronics interface processes the parallel channel outputs of the photo array 10 of the OCDR system into a serial analog signal. The serial analog signal is similar to the echo signal of an ultrasound transducer in that it carries image brightness information and image depth information in a similar manner to a typical echo signal. This enables the ultrasound console 12 to process the serial analog signal outputted by the electronics interface into an image. In addition, the time length and/or frequency of the serial analog signal may be adjusted to better match the time length and/or frequency of a typical echo signal that the ultrasound console 12 is configured to receive.

Figure 2:
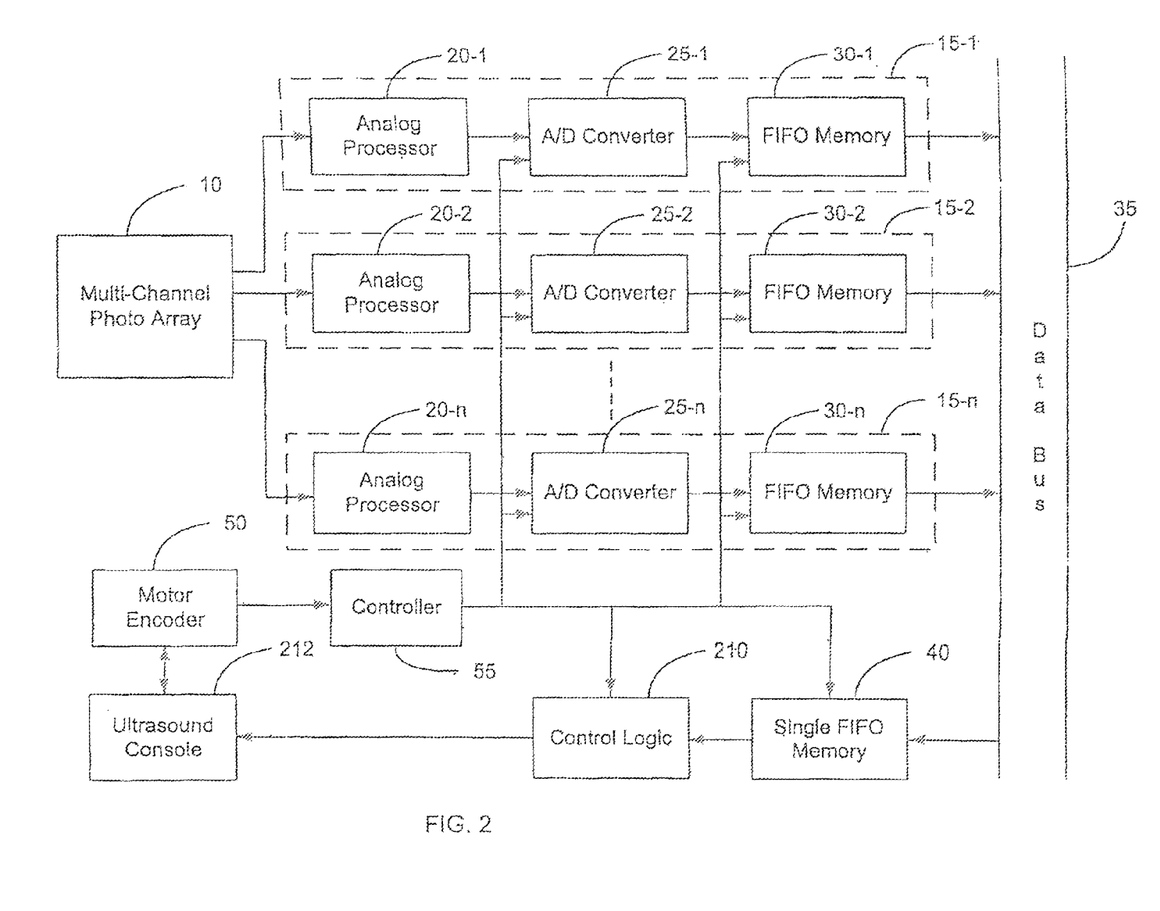
FIG. 2 is a block diagram illustrating another example embodiment of an electronics interface.

FIG. 2 shows an electronics interface according to another example embodiment of the electronics interface. The electronics interface according to this embodiment is coupled between the multi-channel photo array 10 of an OCDR system and an ultrasound console 212 having a digital input. The digital input enables the ultrasound console 212 to receive echo signals that have been digitized by a D/A converter. The digital input of the ultrasound console 212 may use, for example, a Versa Module Eurocard (VME) bus and/or a Peripheral Component Interconnect (PCI) bus to receive digital data.

The electronics interface according to this embodiment includes a control logic 210 in place of the D/A converter 45. The D/A converter 45 is not needed because the ultrasound console 212 has a digital input. The control logic 210 is coupled to the output of the single FIFO memory buffer 40 and the digital input of the ultrasound console 212.

The control logic 210 controls the transfer of the digital data sequence from the single FIFO memory buffer 40 to the digital input of the ultrasound console 212. Preferably, the control logic 210 transfers one digital data sequence for each encoder pulse of the motor encoder 50. For the case in which the digital input of the ultrasound console 212 uses a PCI bus, the control logic 210 may also perform handshaking functions to coordinate the transfer of data from the single FIFO memory buffer 40 to the digital input of the ultrasound console 212.

The ultrasound console 212 according to this embodiment may also include a software-based module for interpreting the digital data sequence received from the electronics interface. For example, the digital data in the digital data sequence may be arranged in order of increasing image depth so that the different data positions in the digital data sequence correspond to different image depths. In this example, the software-based module may translate the different data positions in a received digital data sequence into their corresponding image depths. The digital data and their corresponding image depths may then be inputted to the ultrasound image processor of the ultrasound console 212 to produce an image.

Figure 3:
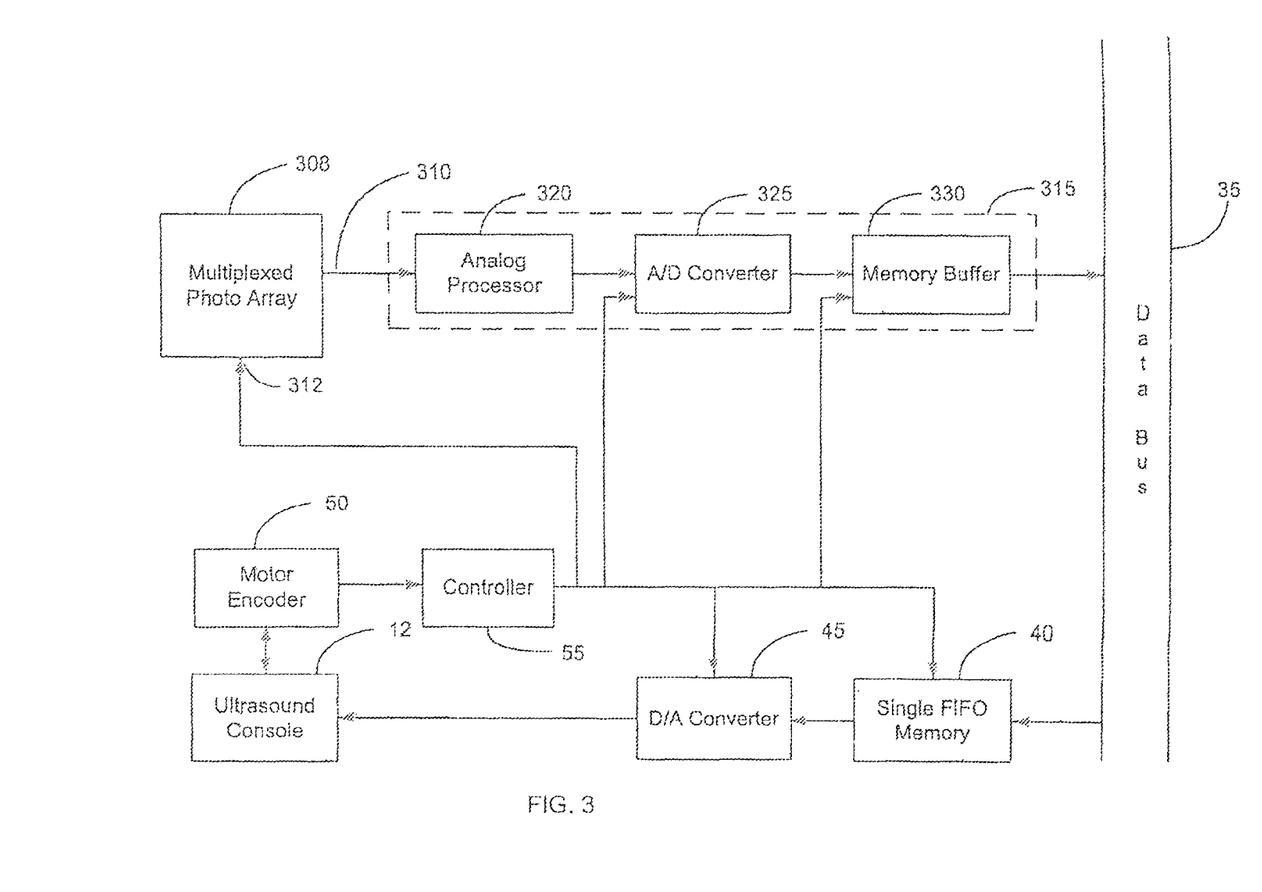
FIG. 3 is a block diagram illustrating an electronics interface coupled between a single-channel multiplexed photo array and an ultrasound console.

FIG. 3 illustrates yet another embodiment of the electronics interface. The electronics interface according to this embodiment is coupled between a multiplexed photo array 308 of an OCDR system and an ultrasound console 12. The multiplexed photo array 308 comprises a plurality of photo detectors (not shown), such as 256 photo detectors. Each photo detector of the multiplexed photo array 308 outputs a signal carrying image brightness information for a certain depth. The multiplexed photo array 308 according to this embodiment further includes a channel output 310 and a control input 312. The output of each one of the photo detectors of the multiplexed photo array 308 can be dynamically coupled to the channel output 310 via a switching network (not shown). The switching network is configured to couple the output of one of the photo detectors to the channel output 310 at a certain time and is controlled by the control input 312.

The electronics interface includes a channel processor 315 coupled to the channel output 310 of the multiplexed photo array 308. The channel processor 315 includes an analog processor 320 and an A/D converter 325. The electronics interface also includes a memory buffer 330, such as a RAM memory or any other kind of memory, coupled to the output of the A/D converter 325. The output of the memory buffer 330 is coupled to the data bus 35 of the electronics interface. The controller 55 of the electronics interface is coupled to the control input 312 of the multiplexed photo array 308. The controller 55 is also coupled to the A/D converter 325, memory buffer 330, D/A converter 45, the single FIFO memory 40, and the motor encoder 50.

When the controller 55 receives a first encoder pulse from the motor encoder 50, the controller 55 instructs the switching network of the multiplexed photo array 308 to sequentially output the signal of each one of the photo detectors to the channel output 310. The analog processor 320 of the channel processor 315 performs analog processing on the channel output 310 in a manner similar to the analog processor 20-$n$ in FIG. 1. The controller 55 instructs the A/D converter 325 to digitize the output of the analog processor 320. Preferably, the controller 55 coordinates the timing of the switching network of the multiplexed photo array 308 and the A/D converter 325 such that the AD converter 325 acquires at least one digital datum from the signal of each one of the photo detectors. The A/D converter 325 writes its digital data into the memory buffer 330. Preferably, the memory buffer 330 stores the received digital data into assigned memory addresses according to their corresponding image depths. The memory buffer 330 may determine the corresponding image depths of the digital data, for example, by having the switching network of the multiplexed photo array 308 sequentially output the signals of the photo detectors in order of increasing image depth, or alternatively, in order of decreasing depth. In other words, the switching network outputs the signals of the photo detectors corresponding to shallower image depths before it outputs the signals of the photo detectors corresponding to deeper image depths.

The memory buffer 330 sequentially writes its digital data to the single FIFO memory buffer 40 via the data bus 35, preferably, in order of increasing image depth. When the controller 55 receives a second (subsequent) encoder pulse from the motor encoder 50, the digital data acquired during the first encoder pulse is outputted to the ultrasound console 12 in serial analog form in a manner similar to the electronics interface of FIG. 1. Alternatively, for the case in which the ultrasound console 12 has a digital input, the digital data may be outputted without the use of a D/A converter 45 to the ultrasound console 12 as a digital data sequence in a manner similar to the electronics interface of FIG. 2.

An advantage of the electronics interface according to this embodiment is that it reduces hardware costs by only requiring one channel processor 325 to process the output of the multiplexed photo array 308. This is because the multiplexed photo array 308 sequentially outputs the signals of its photo detectors on a single channel 310 instead of outputting the signals of its photo detectors on separate parallel channels.

Figure 4:
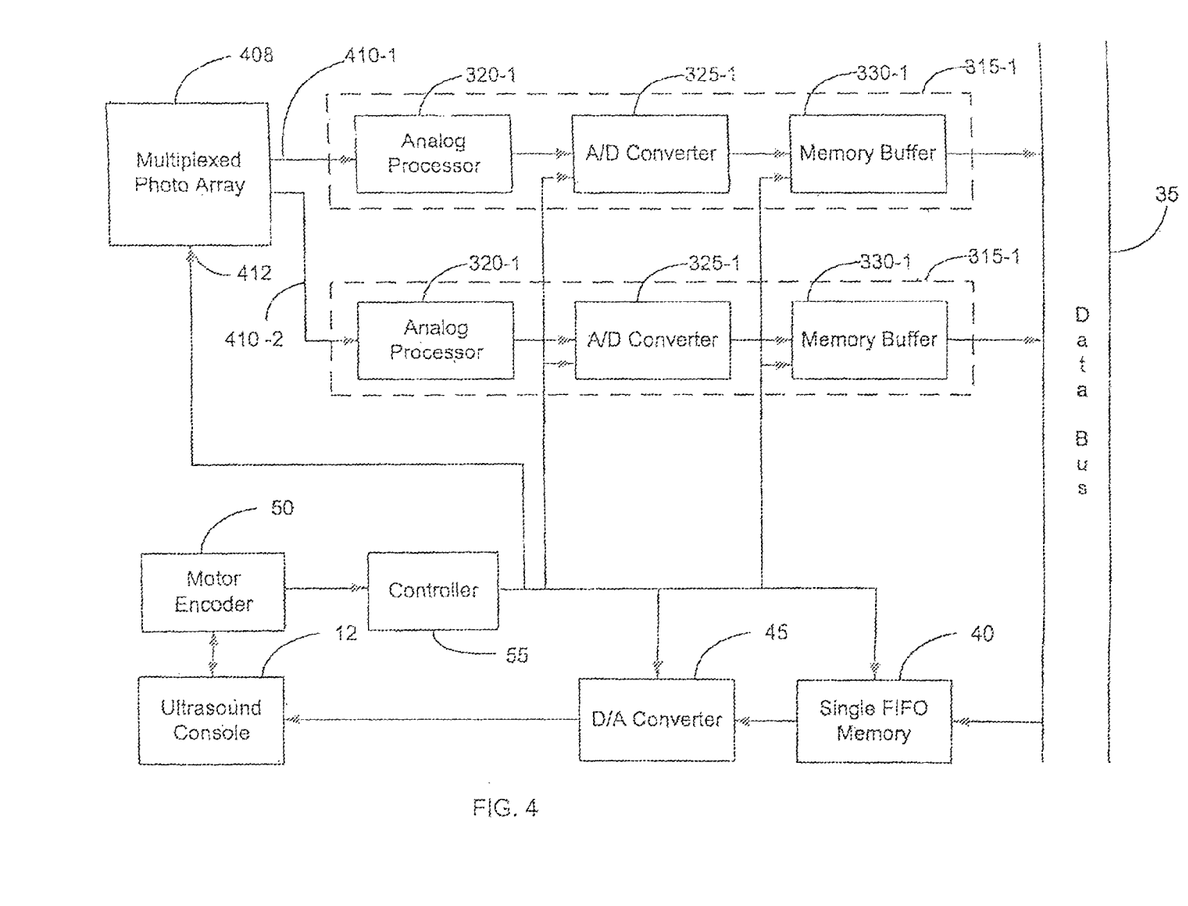
FIG. 4 is a block diagram illustrating an electronics interface coupled between a two-channel multiplexed photo array and an ultrasound console.

FIG. 4 illustrates still another embodiment of the electronics interface which is coupled to a two-channel multiplexed photo array 408. The multiplexed array 408 includes a first channel output 410-1, and a second channel output 410-2. Each one of a first half of the photo detectors of the multiplexed photo array 408 can be dynamically coupled to the first channel output 410-1 via a first switching network (not shown). Each one of a second half of the photo detectors can be dynamically coupled to the second channel 410-2 via a second switching network (not shown).

The electronics interface of FIG. 4 includes a first and second channel processor 315-1, 315-2 coupled to the first and second channel output 410-1, 410-2, respectively. Each channel processor 315-1, 315-2 includes an analog processor 320-1, 320-2, an A/D converter 325-1, 325-2 and a memory buffer 330-1, 330-2. The output of the memory buffer 330-1, 330-2 of each one of the channel processors 315-1, 315-2 is coupled to the data bus 35. Alternatively, the first and second channel processors 315-1, 315-2 may share a common memory buffer. In this alternative case, the output of the A/D converter 325-1, 325-2 of each one of the channel processors 315-1, 315-2 would be coupled to the common memory buffer.

When the controller 55 receives a first encoder pulse from the motor encoder 50, the controller 55 instructs the first switching network of the multiplexed photo array 408 to sequentially output the signal of each one of the first half of the photo detectors to the first channel output 410-1. Similarly, the controller 55 instructs the second switching network to sequentially output the signal of each one of the second half of the photo detectors to the second channel output 410-2. The analog processor 320-1, 320-2 of each one of the channel processors 315-1, 315-2 performs analog processing on the respective channel output 410-1, 410-2. The controller 55 instructs each ND converter 325-1, 325-2 to digitize the output of the respective analog processor 320-1, 320-2. Preferably, the controller 55 coordinates the timing of the first switching network and the A/D converter 325-1 of the first channel processor 315-1 such that the ND converter 325-1 acquires at least one digital datum from the signal of each one of the first half of the photo detectors. Similarly, the controller 55 coordinates the timing of the second switching network and the ND converter 325-2 of the second channel processor 315-2 such that the A/D converter 352-2 acquires at least one digital datum from the signals of each one of the second half of the photo detectors. Each one of the ND converters 325-1, 325-2 writes its digital data into the respective memory buffer 330-1, 330-2. Preferably, each memory buffer 330-1, 330-2 stores its received digital data into assigned memory spaces according to their corresponding image depth.

The memory buffers 330-1, 330-2 sequentially write their digital data to the single FIFO memory buffer 40 via the data bus 35, preferably, in order of increasing image depth. When the controller 55 receives a second (subsequent) encoder pulse from the motor encoder 50, the digital data acquired during the first encoder pulse is outputted to the ultrasound console 12 in serial analog form in a manner similar to the electronics interface of FIG. 1. Alternatively, for the case in which the ultrasound console has a digital input, the digital data may be outputted to the ultrasound console 12 as a digital data sequence in a manner similar to the electronics interface of FIG. 2.

An advantage of the electronics interface according to this embodiment is that it this may achieve higher data read out rates compared with the electronics interface of FIG. 3. This is because the electronics interface according to this embodiment uses two channel processors to simultaneously process two separate outputs of the multiplexed photo array. Thus, while adding to the hardware cost of the electronics interface, additional channel processors may increase the data read out rate of the electronics interface. Those skilled in the art will appreciate that the multiplexed photo array and the electronics interface may include any number of channels.

Figure 5:
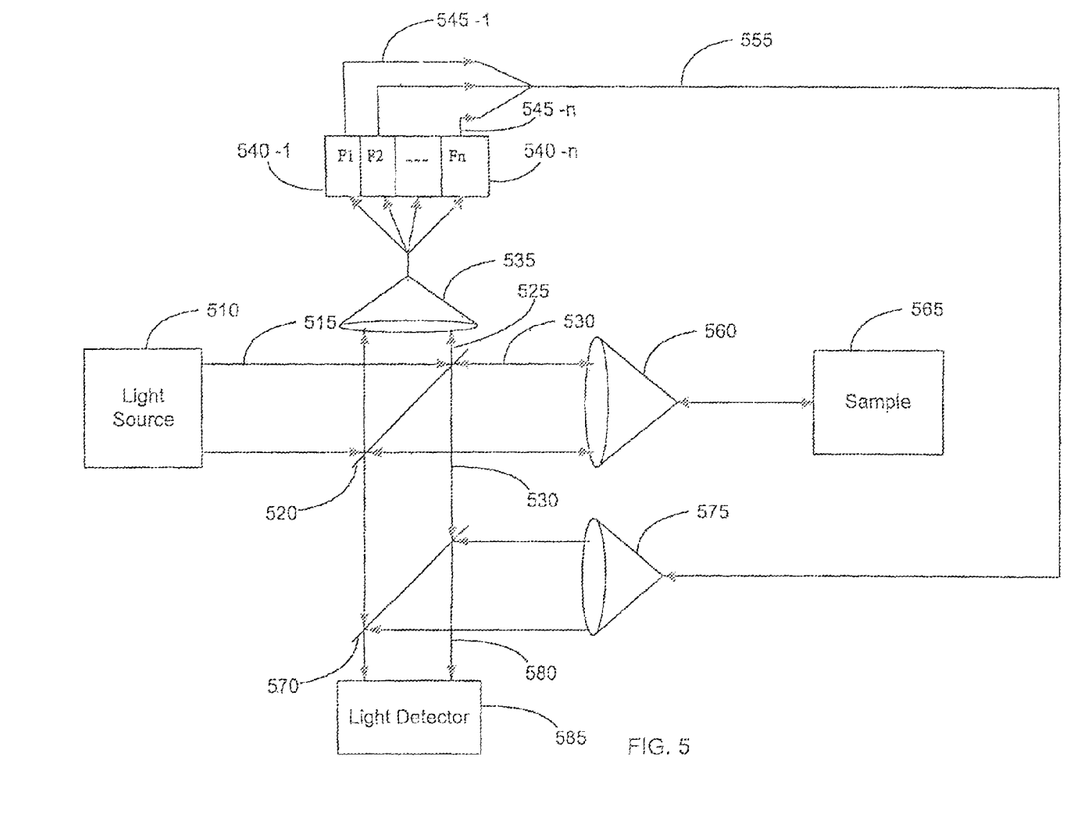
FIG. 5 is a block diagram illustrating an example embodiment of an improved OCDR system.

FIG. 5 shows an example embodiment of an improved OCDR system. The OCDR system includes a light source 510, such as a laser, a beam splitter 520, a beam combiner 570, and plurality of light modulators 540-1 to 540-n. The OCDR system also includes an optical fiber bundle comprising a plurality of optical fibers 545-n, such as 256 optical fibers, where each one of the optical fibers 545-n is coupled to one of the light modulators 540-n. For the sake of simplicity, the reference numeral 540-n refers to any of the light modulators and 545-n refers to any of the optical fibers. Preferably, the light traveling through the optical fibers preceding the light modulators 540-n do not travel in free space or air prior to their being received by the light modulators 540-n. In contrast to grating-based OCDR systems which rely on free space to carry information spatially in the light beam, this embodiment preferably carries information in different frequencies of light, thereby making free space unnecessary. The elimination of a transition from optical fiber to free space improves system efficiency because there is a certain amount of loss at each interface between fiber optic and air. Also, the light traveling from the modulators 540-n to the optical fibers 545-n preferably do not travel in free space. The optical fibers 545-n have different path lengths, which may differ from each other by multiples of, for example, 20 μm. The OCDR system also comprises a first optical coupler 535 positioned between the beam splitter 520 and light modulators 540-n, and a second optical coupler 560 positioned between the beam splitter 520 and a sample 565 to be imaged, e.g., a region of a body. The OCDR system further comprises a third optical coupler 575 positioned between a reference beam optical path 555 and the beam combiner 570, and a light detector 585. The light detector 585 may be, for example, an avalanche photodiode.

During operation, the light source 510 generates a source beam 515. The beam splitter 520 splits the source beam 515 into a reference beam 525 and a sample beam 530. The split may be a 50-50 split or a 10-90 split, in which 90% of the power of the source beam 515 goes into the sample beam 530 and 10% of the power goes into the reference beam 525. The amount of power given to each one of the sample and reference 530, 525 will depend on the application. The second optical coupler 560 directs the sample beam 530 to the sample 565 to be imaged. For example, the sample 565 may be a blood vessel and the second coupler 560 may couple the sample beam 530 to a proximal end of an optical-fiber catheter (not shown), which then transmits the sample beam 530 to the blood vessel. A portion of the sample beam 530 is reflected back from the sample 565 to the second coupler 560. The second coupler 560 directs the reflected sample beam 530 back to the beam splitter 520. The reflected sample beam 530 is then reflected off of the beam splitter 520 to the beam combiner 570.

The first coupler 535 splits the reference beam 525 into a plurality of beams and couples each one of the plurality of beams to one of the light modulators 540-1 to 540-n. Each light modulator 540-n modulates the respective beam at a unique modulation frequency, for example, within an operating frequency range of 10 MHz. In this example embodiment, each light modulator 540-n may be a Lithium Niobate crystal, where a sinusoidal voltage is applied to the crystal to modulate the frequency of the respective beam. Each light modulator 540-n outputs its frequency-modulated beam to one of the optical fibers 545-n. The frequency-modulated beams propagate through their respective optical fiber 545-n and are merged into a frequency-modulated reference beam 555, for example, using a lens (not shown).

The resulting frequency-modulated reference beam 555 contains each modulation frequency of the light modulators 540-n. In addition, each modulation frequency of the frequency-modulated reference beam 555 experiences a slightly different propagation delay path length. This is because the frequency-modulated beams from the light modulators 540-n propagate through optical fibers 545-n of different path lengths before merging into the frequency-modulated reference beam 555. The frequency-modulated reference beam 555 is directed along a reference beam optical path 555 to the third optical coupler 575. The third optical coupler 575 directs the frequency-modulated reference beam 555 to the beam combiner 570, which combines the frequency modulated-reference 555 and the reflected sample beam 530 into a combined beam 580. The resulting combined beam 580 is focused onto the light detector 585, for example, by an optical lens (not shown).

The combined beam 580 preferably carries both image brightness information and image depth information of the sample 565. The image brightness information is provided by the light intensity of combined beam 580. The image depth information is provided by the different modulation frequencies of the combined beam 580. This is because the different modulation frequencies of the frequency-modulated reference beam 555 experience different propagation delay path lengths due to the different path lengths of the optical fibers 545-$n$. As a result, the different modulation frequencies of the frequency-modulated reference beam 555 constructively interfere with portions of the reflected sample beam 530 reflected from different depths in the sample 565. Thus, the depth information contained in the combined beam 580 is a function of modulation frequency.

The light detector 585 detects the combined beam 580 and outputs a detector signal (not shown) that carries image brightness information at multiple image depths, where each image depth corresponds to a different modulation frequency. Therefore, the image depth information contained in the detector signal may be resolved by tuning a conventional radio tuner to the desired modulation frequency. This can be achieved using a sweep oscillator and standard detection hardware such as heterodyne detection.

An advantage of the OCDR system according to this embodiment is that it focuses the light energy of the combined beam 580 onto one light detector, instead of wasting a portion of the light energy due to spacing between photo detectors in a photo array. In addition, the OCDR system enables the use of avalanche mode photodiodes, which are far more sensitive than standard photo-elements.

By using multiple frequency modulators, only one electronic channel needs to be constructed for processing the imaging information. The use of a single electronic channel dramatically reduces the size and complexity of the electronics interface. In addition, the present invention contemplates high-speed electronic processing such that video rates, and therefore, real time viewing, can be realized.

Figure 6:
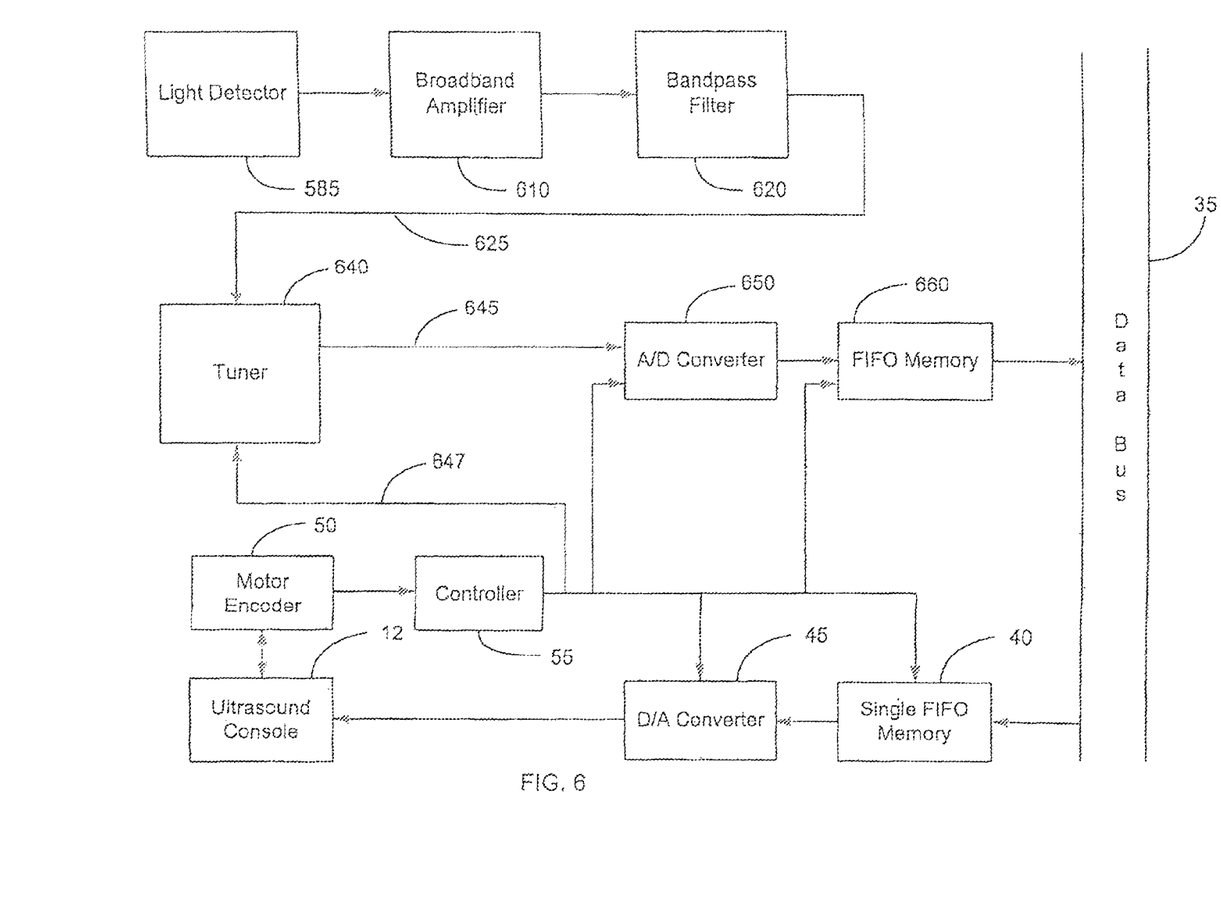
FIG. 6 is a block diagram illustrating an electronics interface coupled between the OCDR system of FIG. 5 and an ultrasound console.

FIG. 6 shows an electronics interface coupled between the light detector 585 of the OCDR system of FIG. 5 and an ultrasound console 12. The electronics interface includes a broadband amplifier 610 coupled to the light detector 585 of the OCOR system, a broadband filter 620 coupled to the output of the broadband amplifier 610, and a tuner 640 coupled to the output of the broadband filter 620. For example, the tuner 640 may be a radio tuner and the broadband filter 620 may be a bandpass filter. The tuner 640 is coupled also to lines 645 and 647. The electronics interface further includes an A/D converter 650 coupled to the tuner 640 via line 645, and a FIFO memory 660 coupled to the output of the A/D converter 650. The output of the FIFO memory 660 is coupled to a data bus 35. A single FIFO memory 40 is coupled to the data bus 35. The single FIFO memory 40 is coupled to a D/A converter 45. The D/A converter 45 is coupled to the ultrasound console 12. The ultrasound console 12 is coupled to a motor encoder 50. The controller 55 in this example embodiment is coupled to the motor encoder 50, tuner 640, A/D converter 650, FIFO memory 660, D/A converter 45 and the single FIFO memory 40. The controller 55 controls the tuned frequency of the tuner 640 via line 647.

During operation, the broadband amplifier 610 amplifies the detector signal from the light detector 585 and passes the amplified signal to the broadband filter 620. The broadband filter 620 passes the portion of the amplified detector signal that is within the modulation frequency range of the OCDR system to the tuner 640. The tuner 640 is configured to tune to one of the modulation frequencies of the detector signal at a time.

When the controller 55 receives a first encoder pulse from the motor encoder 50, the controller 55 instructs the tuner 640 to sweep its tuning frequency across the entire modulation frequency range of the OCDR system. This causes the tuner 640 to sequentially tune to each one of the modulation frequencies of the detector signal. The A/D converter 650 digitizes the tuned detector signal from the tuner 640. Preferably, the controller 55 coordinates the timing of the tuner 640 and the A/D converter 650 such that the A/D converter 650 acquires at least one digital datum for each tuned modulation frequency of the detector signal. The A/D converter 650 writes its digital data to the FIFO memory 660. Preferably, the A/D converter 650 writes its digital data to the FIFO memory 660 in order of increasing image depth. This may be done, for example, by having the lower modulation frequencies of the detector signal correspond to shallower image depths and the higher modulation frequencies of the detector signal correspond to the deeper image depths, and by sweeping the tuning frequency of the tuner 640 from a low frequency to a high frequency.

The FIFO memory 660 sequentially writes its digital data to the single FIFO memory buffer 40 via the data bus 35, preferably, in order of increasing image depth. When the controller 55 receives a second (subsequent) encoder pulse from the motor encoder 50, the digital data acquired during the first encoder pulse is outputted to the ultrasound console 12 in serial analog form in a manner similar to the electronics interface of FIG. 1. Alternatively, for the case in which the ultrasound console 12 has a digital input, the digital data may be outputted to the ultrasound console 12 as a digital data sequence in a manner similar to the electronics interface of FIG. 2.

Figure 7:
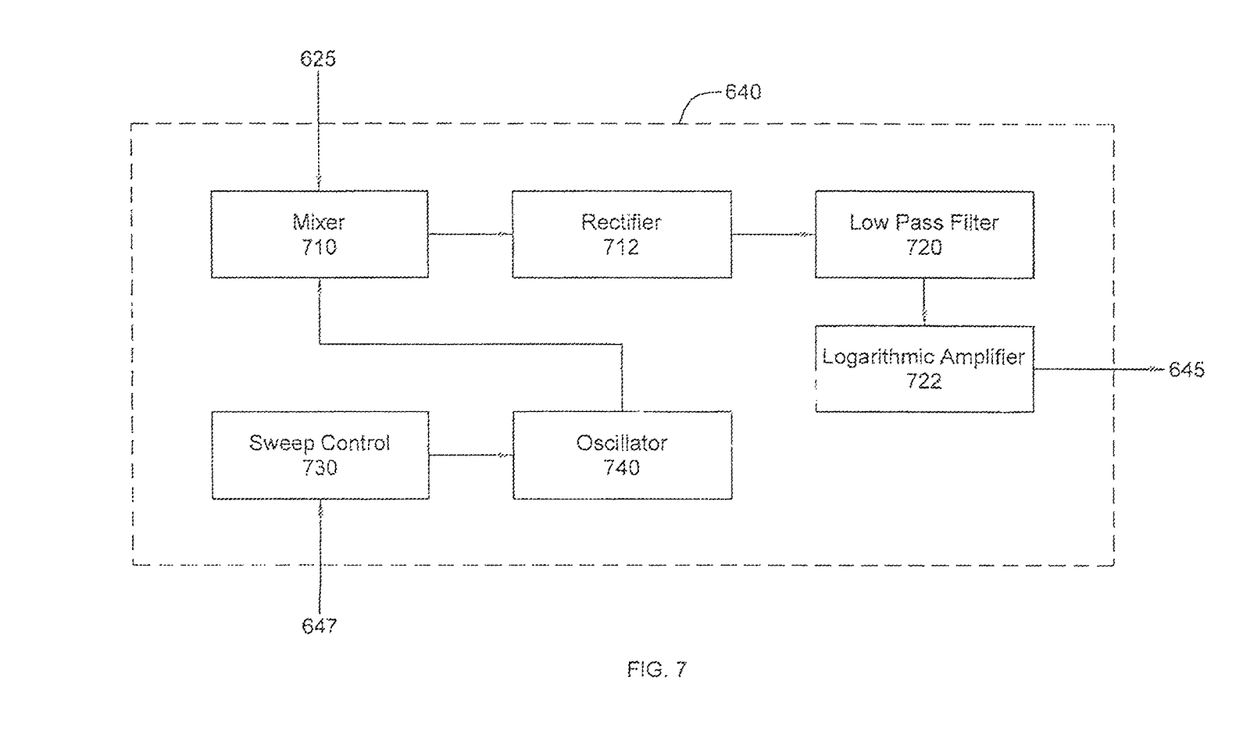
FIG. 7 is a block diagram illustrating an exemplary mixer.

FIG. 7 illustrates a block diagram of an exemplary tuner 640 that may be used in the electronics interface of FIG. 6. The tuner 640 includes a sweep control 730 coupled to the controller 55 by line 647, and a local oscillator 740 coupled to the output of the sweep control 730. The sweep control 730 varies the frequency of the local oscillator 740 based on the control signals from the controller 55 over line 647. The tuner 640 further includes a mixer 710 coupled to the output of the oscillator 740 and to the output 625 of the broadband filter 620.

The output of the mixer 710 is coupled to a rectifier 712, which is coupled to a low pass filter 720. The mixer 710 down converts, i.e., translates, the modulation frequencies of the detector signal to lower frequencies by mixing, i.e., multiplying, the output 625 of the broadband filter 620 with the output of the oscillator 740. The low pass filter 720 is configured to pass one of the down-converted modulation frequencies of the detector signal at a time. The frequency of the local oscillator 740 controls which one of the down-converted modulation frequencies of the detector signal is passed through the low pass filter 720. Thus, the tuner 640 can be tuned to different modulation frequencies of the detector signal by varying the frequency of the oscillator 740 using the sweep control 730. The low pass filter 720 is coupled to a logarithmic amplifier 722.

Also, it is contemplated that any embodiment described in this patent specification can be modified such that, for example, the number of any of the components can be increased or decreased as desired. Further, it is contemplated that features shown in one embodiment may be added to those of another embodiment, or features shown in one embodiment may be deleted, as desired. Any one or more of the features depicted in any of the figures, or described in the accompanying text, may be interchanged with that of another figure to form still other embodiments.

While various embodiments of the application have been described, it will be apparent to those of ordinary skill in the art that many embodiments and implementations are possible that are within the scope of the invention. Therefore, the invention is not to be restricted or limited except in accordance with the following claims and their equivalents.

The invention claimed is:

1. A system for imaging body tissue comprising:
    a beam splitter configured and arranged to receive a light beam and generate a reference light beam and a sample light beam from the light beam;
    a plurality of modulators, each modulator configured and arranged to receive a portion of the reference light beam, each modulator configured and arranged to modulate the portion of the reference light beam received by that modulator at a unique modulation frequency, wherein the modulation by the plurality of modulators forms a plurality of modulated reference light beams;
    a beam combiner physically separated from the beam splitter and configured and arranged to receive the sample light beam reflected from a region of body tissue to be imaged and to receive the plurality of modulated reference light beams and to generate a combined light beam from the reflected sample light beam and the plurality of modulated reference light beams;
    a light detector configured and arranged to receive the combined light beam and output a detector signal based on the combined light beam;
    a tuner configured and arranged to receive the detector signal and to be tunable over a range of the unique modulation frequencies of the plurality of modulated reference light beams; and
    a controller configured and arranged to sequentially tune the tuner to each of the unique modulation frequencies one at a time with the tuner consequently converting the detector signal to a tuner output signal.

2. The system of claim 1, further comprising a light source configured and arranged to produce the light beam.

3. The system of claim 1, wherein the system is configured and arranged to provide a different propagation delay to each of the modulated reference light beams.

4. The system of claim 1, further comprising a first light coupler configured and arranged to receive the reference light beam and a plurality of first optical fibers configured and arranged to each receive a portion of the reference light beam from the first light coupler and to deliver that portion of the reference light beam to a corresponding one of the plurality of modulators.

5. The system of claim 4, further comprising a plurality of second optical fibers configured and arranged to each receive a different one of the modulated reference light beams from a corresponding one of the plurality of modulators.

6. The system of claim 5, wherein each of the second optical fibers is configured and arranged to provide a different propagation delay to the modulated reference light beam received by that second optical fiber.

7. The system of claim 1, further comprising a second light coupler configured and arranged to receive the sample beam and to direct the sample beam to the region of body tissue to be imaged.

8. The system of claim 1, wherein the system is configured and arranged so that an amplitude of the tuner output signal provides image brightness information and a time position of the tuner output signal provides image depth information.

9. The system of claim 1, further comprising a console configured and arranged to produce and display an image based on the tuner output signal.

10. The system of claim 9, wherein the console is an ultrasound console.

11. A method of imaging body tissue, the method comprising:
    providing a source beam;
    splitting the source beam into a reference beam and a sample beam using a beam splitter;
    splitting the reference beam into a plurality of intermediate beams;
    directing each intermediate beam to a different one of a plurality of light modulators, each light modulator modulating the intermediate beam directed to that light modulator at a different modulation frequency, each modulation frequency corresponding to a different image depth;
    directing the sample beam at a sample;
    combining the sample beam, after being directed to the sample, with the plurality of modulated intermediate beams to form a combined beam using a beam combiner that is physically separated from the beam splitter;
    converting the combined beam into a detector signal using a light detector; and
    generating a tuner output signal from the detector signal using a tuner that is tuned to each of the different modulation frequencies one at a time, wherein an amplitude of the tuner output signal provides image brightness information and a time position within the tuner output signal provides image depth information.

12. The method of claim 11, further comprising generating and displaying an image based on the tuner output signal.

13. The method of claim 11, wherein generating a tuner output signal comprises sequentially tuning the tuner to each of the plurality of the different modulation frequencies in an order of the modulation frequencies corresponding to image depth to generate the tuner output signal.

14. The method of claim 11, further comprising directing the modulated intermediate light beams along different paths to provide different propagation delays to the modulated intermediate light beams.

15. The method of claim 11, converting the tuner output signal into a digital output signal.

16. The system of claim 1, further comprising a band pass filter disposed between the light detector and the tuner.

17. The system of claim 1, wherein the light detector is a single photodetector.

18. The system of claim 1, further comprising a motor encoder coupled to the controller.

19. The system of claim 1, wherein the beamsplitter directs less than 50% of power of the light beam into the reference light beam.

20. The system of claim 2, wherein the light source is a single light source.

* * * * *